(12) United States Patent
Levanon

(10) Patent No.: US 10,052,056 B2
(45) Date of Patent: Aug. 21, 2018

(54) SYSTEM FOR CONFIGURING COLLECTIVE EMOTIONAL ARCHITECTURE OF INDIVIDUAL AND METHODS THEREOF

(71) Applicant: BEYOND VERBAL COMMUNICATION LTD, Tel-Aviv (IL)

(72) Inventor: Yoram Levanon, Ramat Hasharon (IL)

(73) Assignee: BEYOND VERBAL COMMUNICATION LTD, Tel-Aviv (IL)

( * ) Notice: Subject to any disclaimer, the term of this patent is extended or adjusted under 35 U.S.C. 154(b) by 0 days.

(21) Appl. No.: 15/507,872

(22) PCT Filed: Aug. 31, 2015

(86) PCT No.: PCT/IL2015/050875
§ 371 (c)(1),
(2) Date: Mar. 1, 2017

(87) PCT Pub. No.: WO2016/035069
PCT Pub. Date: Mar. 10, 2016

(65) Prior Publication Data
US 2017/0287473 A1   Oct. 5, 2017

Related U.S. Application Data

(60) Provisional application No. 62/044,346, filed on Sep. 1, 2014.

(51) Int. Cl.
*G10L 25/63* (2013.01)
*A61B 5/16* (2006.01)
(Continued)

(52) U.S. Cl.
CPC .............. *A61B 5/16* (2013.01); *A61B 5/7246* (2013.01); *A61B 5/7275* (2013.01); *G10L 17/26* (2013.01); *G10L 25/63* (2013.01)

(58) Field of Classification Search
CPC ....................................................... G10L 25/63
See application file for complete search history.

(56) References Cited

U.S. PATENT DOCUMENTS 5,054,085 A * 10/1991 Meisel .................... G10L 15/02
704/207
6,148,287 A * 11/2000 Yamakita ............ H04M 3/5307
379/88.04
(Continued)

FOREIGN PATENT DOCUMENTS

| EP | 0251576 A2 | 1/1988 |
| WO | 2008/053359 A2 | 5/2008 |
| WO | 2016/035069 A1 | 3/2016 |

OTHER PUBLICATIONS

International Search Report for PCT/IL2015/050875, dated Jan. 5, 2016.
(Continued)

*Primary Examiner* — Eric Yen

(57) ABSTRACT

The present invention provides a system and method for configuring collective emotional architecture of an individual. The system comprising an input module, adapted to receive voice input and orientation reference selected from a group consisting of: date, time, location, and any combination thereof; a personal collective emotionbase, the emotionbase comprising benchmark tones and benchmark emotional attitudes (BEA) while each of the benchmark tones corresponds to a specific BEA and at least one processor in communication with a computer readable medium (CRM). The processor executes a set of operations received from the CRM.

38 Claims, 4 Drawing Sheets

(51) Int. Cl.
   *A61B 5/00*   (2006.01)
   *G10L 17/26*  (2013.01)

(56) References Cited

U.S. PATENT DOCUMENTS

| | | | | |
|---|---|---|---|---|
| 6,223,156 | B1* | 4/2001 | Goldberg | G10L 15/24 |
| | | | | 379/88.01 |
| 6,878,111 | B2 | 4/2005 | Kenknight et al. | |
| 7,127,403 | B1* | 10/2006 | Saylor | H04M 3/42153 |
| | | | | 704/275 |
| 7,917,366 | B1 | 3/2011 | Levanon et al. | |
| 8,078,470 | B2 | 12/2011 | Levanon et al. | |
| 9,202,520 | B1* | 12/2015 | Tang | G11B 27/00 |
| 9,378,730 | B1* | 6/2016 | Tickner | G10L 15/02 |
| 2003/0050777 | A1* | 3/2003 | Walker, Jr. | G10L 15/30 |
| | | | | 704/235 |
| 2003/0120489 | A1* | 6/2003 | Krasnansky | G10L 19/0018 |
| | | | | 704/235 |
| 2003/0167167 | A1* | 9/2003 | Gong | G10L 15/22 |
| | | | | 704/250 |
| 2003/0182123 | A1* | 9/2003 | Mitsuyoshi | G06K 9/00335 |
| | | | | 704/270 |
| 2004/0170258 | A1* | 9/2004 | Levin | H04M 1/274575 |
| | | | | 379/88.01 |
| 2004/0249634 | A1* | 12/2004 | Degani | G10L 17/26 |
| | | | | 704/207 |
| 2007/0168337 | A1* | 7/2007 | Onodera | G06F 17/3053 |
| 2008/0049908 | A1* | 2/2008 | Doulton | H04M 3/4936 |
| | | | | 379/88.14 |
| 2008/0154601 | A1* | 6/2008 | Stifelman | G10L 15/22 |
| | | | | 704/251 |
| 2008/0270123 | A1* | 10/2008 | Levanon | G10L 17/26 |
| | | | | 704/200.1 |
| 2009/0018832 | A1* | 1/2009 | Mukaigaito | G10L 15/1815 |
| | | | | 704/251 |
| 2009/0048832 | A1* | 2/2009 | Terao | G10L 15/26 |
| | | | | 704/235 |
| 2009/0254342 | A1* | 10/2009 | Buck | G10L 15/222 |
| | | | | 704/233 |
| 2011/0301952 | A1* | 12/2011 | Koshinaka | G10L 15/32 |
| | | | | 704/235 |
| 2012/0296642 | A1* | 11/2012 | Shammass | G10L 25/63 |
| | | | | 704/211 |
| 2013/0030812 | A1* | 1/2013 | Kim | G06Q 50/01 |
| | | | | 704/270 |
| 2013/0038756 | A1* | 2/2013 | Cheng | H04N 21/42201 |
| | | | | 348/231.99 |
| 2013/0325448 | A1* | 12/2013 | Levien | G10L 19/00 |
| | | | | 704/201 |
| 2014/0002464 | A1* | 1/2014 | Furukawa | G10L 21/10 |
| | | | | 345/474 |
| 2014/0025385 | A1* | 1/2014 | Atri | H04N 21/42203 |
| | | | | 704/270 |
| 2014/0140497 | A1* | 5/2014 | Ripa | H04M 3/5133 |
| | | | | 379/265.06 |
| 2018/0061415 | A1* | 3/2018 | Penilla | G10L 15/22 |

OTHER PUBLICATIONS

Written Opinion of the International Search Authority for PCT/IL2015/050875, dated Jan. 5, 2016.
International Preliminary Report on Patentability (Chapter II) for PCT/IL2015/050875, dated Aug. 17, 2016.

* cited by examiner

SYSTEM FOR CONFIGURING COLLECTIVE EMOTIONAL ARCHITECTURE OF INDIVIDUAL AND METHODS THEREOF

CROSS-REFERENCE TO RELATED APPLICATIONS

This application is a U.S. National Phase filing under 35 U.S.C. 371 of International (PCT) Patent Application No. PCT/IL2015/050875, filed Aug. 31, 2015, which claims priority from U.S. Provisional Patent Application No. 62/044,346, filed Sep. 1, 2014, both of which are incorporated by reference in their entirety.

FIELD OF THE INVENTION

The present invention relates to methods and system for configuring collective emotional architecture of an individual by evaluating manifestations of physiological change in the human voice. More specifically, the present invention relates to methods and system for configuring collective emotional architecture of an individual.

BACKGROUND OF THE INVENTION

Recent technologies have enabled the indication of emotional attitudes of an individual, either human or animal, and linking them to one's voice intonation. For example, U.S. Pat. No. 8,078,470 discloses means and method for indicating emotional attitudes of a individual, either human or animal, according to voice intonation. The invention also discloses a system for indicating emotional attitudes of an individual comprising a glossary of intonations relating intonations to emotions attitudes. Furthermore, U.S. Pat. No. 7,917,366 discloses a computerized voice-analysis device for determining an SHG profile (as described therein, such an SHG profile relates to the strengths (e.g., relative strengths) of three human instinctive drives). Of note, the invention may be used for one or more of the following: analyzing a previously recorded voice sample; real-time analysis of voice as it is being spoken; combination voice analysis that is, a combination of: (a) previously recorded and/or real-time voice; and (b) answers to a questionnaire.

Emotional well-being is a term that links physical health to the emotional state of an individual. Mental and emotional well-being is essential to overall health. On the positive side, enhanced emotional well-being is seen to contribute to upward spirals in increasing coping ability, self-esteem, performance and productivity at work, meaningful contributions to ones community, and even longevity. Early childhood experiences have lasting, measurable consequences later in life; therefore, fostering emotional well-being from the earliest stages of life helps build a foundation for overall health and well-being. Anxiety, mood (e.g., depression) and impulse control disorders are associated with a higher probability of risk behaviors (e.g., tobacco, alcohol and other drug use, risky sexual behavior), intimate partner and family violence, many other chronic and acute conditions (e.g., obesity, diabetes, cardiovascular disease, HIV/STIs), and premature death.

Several systems for assessing and improving well-being have been presented. For example, EP patent No. 251,576 discloses a system and method for reducing the effects of negative emotional states by performing physiological measurements of a user with wearable. In another example, U.S. Pat. No. 6,878,111 discloses a system for measuring subjective well-being by receiving data or input that reflects an individual's subjective well-being and creating trends with a correlation module adapted to correlate and compare subjective and/or objective data. None of the cited above patent appear to collect, store and analyze the received data. None of the cited above patent appear to configure collective emotional architecture of an individual based on ongoing activity analysis of three neurotransmitter loops, or SHG profile.

In light of the above, there is a long term unmet need to provide methods and system for implementing analysis of voice intonations as personal psychological tools by configuring a personal emotionbase to monitor one's physical, mental and emotional well-being, and subsequently significantly improve them.

SUMMARY OF THE INVENTION

It is hence one object of this invention to disclose a system for configuring collective emotional architecture of an individual by evaluating manifestations of physiological change in the human voice, said system comprising (1) an input module, said input module is adapted to receive voice input and orientation reference selected from a group consisting of date, time, location, and any combination thereof; (2) a personal collective emotionbase; said emotionbase comprising benchmark tones and benchmark emotional attitudes (BEA), each of said benchmark tones corresponds to a specific BEA; (3) at least one processor in communication with a computer readable medium (CRM), said processor executes a set of operations received from said CRM, said set of operations comprising steps of (a) obtaining a signal representing sound volume as a function of frequency from said volume input; (b) processing said signal so as to obtain voice characteristics of said individual, said processing includes determining a Function A; said Function A being defined as the average or maximum sound volume as a function of sound frequency, from within a range of frequencies measured in said volume input; said processing further includes determining a Function B; said Function B defined as the averaging, or maximizing of said function A over said range of frequencies and dyadic multiples thereof; (c) comparing said voice characteristics to said benchmark tones; and (d) allocating to said voice characteristics at least one of said BEAs corresponding to said benchmark tones. It is in the core of the invention wherein said set of operations additionally comprises a step of assigning said orientation reference to said allocated at least one of said BEAs.

It is a further object of the present invention to provide a system wherein said set of operations additionally comprises a step of archiving said assigned referenced emotional attitudes.

It is a further object of the present invention to provide a system wherein said set of operations additionally comprises a step of matching said archived assigned referenced emotional attitude with predefined situations.

It is a further object of the present invention to provide a system wherein said set of operations additionally comprises a step of predicting emotional attitude according to records of said matching.

It is a further object of the present invention to provide a system wherein said set of operations additionally comprises a step of prompting actions relevant to said predicted emotional attitudes.

It is a further object of the present invention to provide a system wherein said system additionally comprises an output module; said output module is adapted to provide said individual a feedback regarding at least one selected from a group consisting of: his emotional attitude, suggestions how to change his emotional attitude; suggestions how to avoid a specific emotional attitude.

It is a further object of the present invention to provide a system wherein said operation of processing comprises identifying at least one dominant tone, and attributing an emotional attitude to said individual based on said at least one dominant tone.

It is a further object of the present invention to provide a system wherein said operation of processing comprises calculating a plurality of dominant tones, and comparing said plurality of dominant tones to a plurality of normal dominant tones specific to a word or set of words pronounced by said individual so as to indicate at least one emotional attitude of said individual.

It is a further object of the present invention to provide a system wherein said range of frequencies are between 120 Hz and 240 Hz and all dyadic multiples thereof.

It is a further object of the present invention to provide a system wherein said operation of comparing comprises calculating the variation between said voice characteristics and tone characteristics related to said reference tones.

It is a further object of the present invention to provide a system wherein said benchmark emotional attitudes (BEA) are analyzed by evaluating manifestations of physiological change in the human voice; said evaluation is based on ongoing activity analysis of three neurotransmitter loops, or SHG profile.

It is a further object of the present invention to provide a system wherein said system is used for monitoring of risk behaviors; said risk behaviors are selected from a group consisting of: tobacco, alcohol, drug use, eating disorders, gambling addiction, risky sexual behavior, shopping addiction; any other impulse control disorders and addictions and any combination thereof.

It is a further object of the present invention to provide a system wherein said system is used for managing of risk behaviors; said risk behaviors are selected from a group consisting of: tobacco, alcohol, drug use, eating disorders, gambling addiction, risky sexual behavior, shopping addiction; any other impulse control disorders and addictions and any combination thereof.

It is a further object of the present invention to provide a system wherein said system is used for monitoring of anxiety, mood (e.g., depression) and impulse control disorders; and any combination thereof.

It is a further object of the present invention to provide a system wherein said system is used for managing of anxiety, mood (e.g., depression) and impulse control disorders; and any combination thereof.

It is a further object of the present invention to provide a system wherein said system is used for monitoring of chronic and acute conditions; said chronic and acute conditions are selected from a group consisting of: obesity, diabetes, cardiovascular disease, HIV/STIs; any other chronic and acute conditions and any combination thereof.

It is a further object of the present invention to provide a system wherein said system is used for managing of chronic and acute conditions; said chronic and acute conditions are selected from a group consisting of: obesity, diabetes, cardiovascular disease, HIV/STIs; any other chronic and acute conditions and any combination thereof.

It is an object of this invention to disclose a method for creating collective emotional architecture of an individual, said method comprising steps of (1) receiving voice input and an orientation reference selected from a group consisting of date, time, location, and any combination thereof; (2) obtaining an emotionbase; said emotionbase comprising benchmark tones and benchmark emotional attitudes (BEA), each of said benchmark tones corresponds to a specific BEA; (3) at least one processor in communication with a computer readable medium (CRM), said processor executes a set of operations received from said CRM; said set of operations are (a) obtaining a signal representing sound volume as a function of frequency from said volume input; (b) processing said signal so as to obtain voice characteristics of said individual, said processing includes determining a Function A; said Function A being defined as the average or maximum sound volume as a function of sound frequency, from within a range of frequencies measured in said volume input; said processing further includes determining a Function B; said Function B defined as the averaging, or maximizing of said function A over said range of frequencies and dyadic multiples thereof; (c) comparing said voice characteristics to said benchmark tones; and (d) allocating to said voice characteristics at least one of said BEAs corresponding to said benchmark tones. It is in the core of the invention wherein said method additionally comprises a step of assigning said orientation reference to said allocated at least one of said BEAs.

It is an object of this invention to disclose a method wherein said method additionally comprises a step of archiving said assigned referenced emotional attitudes.

It is an object of this invention to disclose a method wherein said method additionally comprises a step of matching said archived assigned referenced emotional attitude with predefined situations.

It is an object of this invention to disclose a method wherein said method additionally comprises a step of predicting emotional attitude according to records of said matching.

It is an object of this invention to disclose a method wherein said method additionally comprises a step of prompting actions relevant to said predicted emotional attitudes.

It is an object of this invention to disclose a method wherein said method additionally comprises a step of providing said individual a feedback regarding at least one selected from a group consisting of one's emotional attitude, suggestions how to change one's emotional attitude; suggestions how to avoid a specific emotional attitude.

It is an object of this invention to disclose a method wherein said step of processing comprises identifying at least one dominant tone, and attributing an emotional attitude to said individual based on said at least one dominant tone.

It is an object of this invention to disclose a method wherein said step of processing comprises calculating a plurality of dominant tones, and comparing said plurality of dominant tones to a plurality of normal dominant tones specific to a word or set of words pronounced by said individual so as to indicate at least one emotional attitude of said individual.

It is an object of this invention to disclose a method wherein said range of frequencies are between 120 Hz and 240 Hz and all dyadic multiples thereof.

It is an object of this invention to disclose a method wherein said step of comparing comprises calculating the variation between said voice characteristics and tone characteristics related to said reference tones.

It is a further object of the present invention to disclose a method wherein said benchmark emotional attitudes (BEA) are analyzed by evaluating manifestations of physiological change in the human voice; said evaluation is based on ongoing activity analysis of three neurotransmitter loops, or SHG profile.

It is an object of this invention to disclose a method wherein said system is used for monitoring of risk behaviors; said risk behaviors are selected from a group consisting of: tobacco, alcohol, drug use, eating disorders, gambling addiction, risky sexual behavior, shopping addiction; any other impulse control disorders and addictions and any combination thereof.

It is an object of this invention to disclose a method wherein said system is used for managing of risk behaviors; said risk behaviors are selected from a group consisting of: tobacco, alcohol, drug use, eating disorders, gambling addiction, risky sexual behavior, shopping addiction; any other impulse control disorders and addictions and any combination thereof.

It is an object of this invention to disclose a method wherein said system is used for monitoring of anxiety, mood (e.g., depression) and impulse control disorders; and any combination thereof.

It is an object of this invention to disclose a method wherein said system is used for managing of anxiety, mood (e.g., depression) and impulse control disorders; and any combination thereof.

It is an object of this invention to disclose a method wherein said system is used for monitoring of chronic and acute conditions; said chronic and acute conditions are selected from a group consisting of: obesity, diabetes, cardiovascular disease, HIV/STIs; any other chronic and acute conditions and any combination thereof.

It is an object of this invention to disclose a method wherein said system is used for managing of chronic and acute conditions; said chronic and acute conditions are selected from a group consisting of: obesity, diabetes, cardiovascular disease, HIV/STIs; any other chronic and acute conditions and any combination thereof.

BRIEF DESCRIPTION OF THE FIGURES

In the following detailed description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention. The present invention may be practiced according to the claims without some or all of these specific details. For the purpose of clarity, technical material that is known in the technical fields related to the invention has not been described in detail so that the present invention is not unnecessarily obscured.

DETAILED DESCRIPTION OF THE INVENTION

Figure 1:
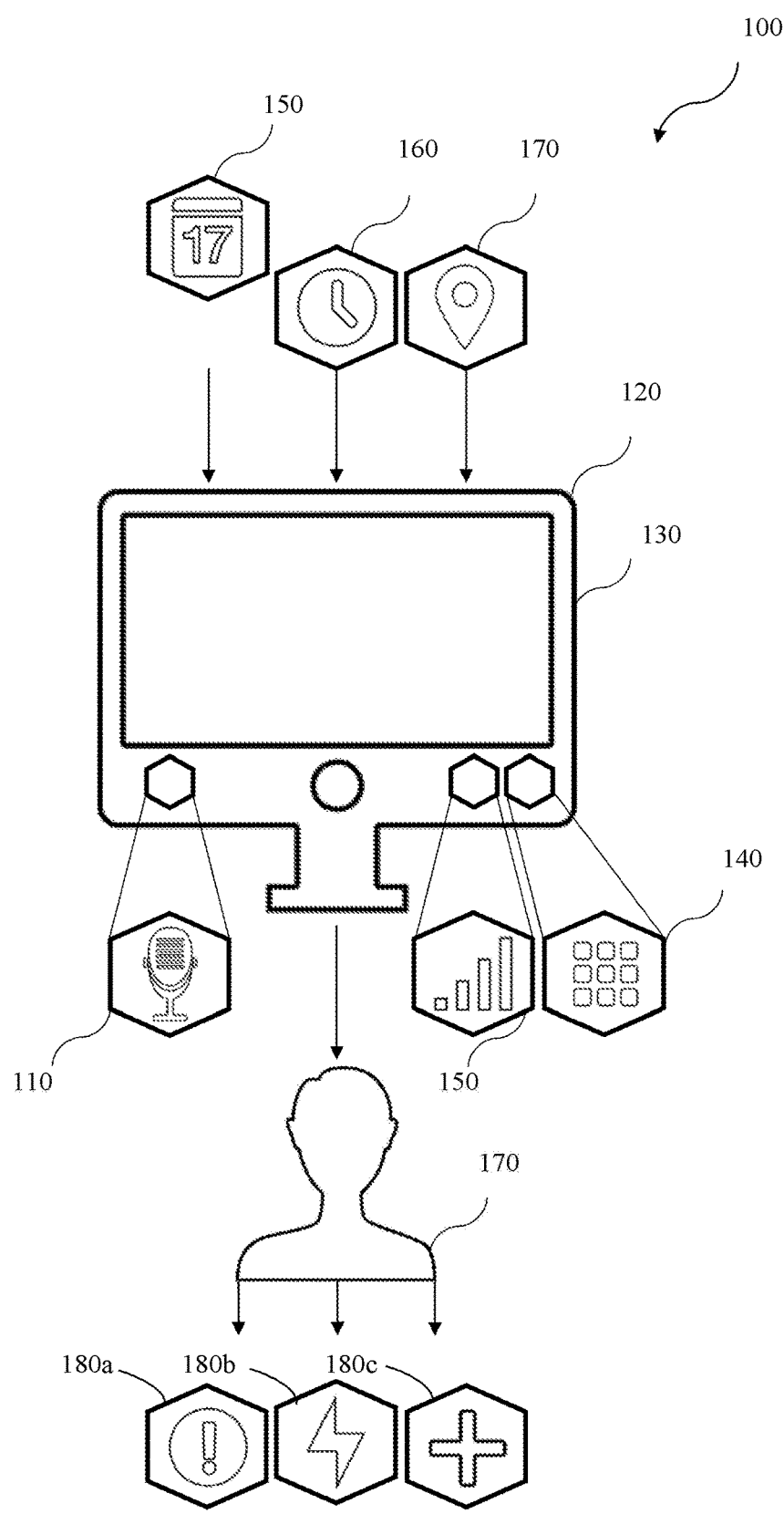
FIG. 1 schematically presents a system according to the present invention.

In the following detailed description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention. The present invention may be practiced according to the claims without some or all of these specific details. For the purpose of clarity, technical material that is known in the technical fields related to the invention has not been described in detail so that the present invention is not unnecessarily obscured.

The term "word" refers in the present invention to a unit of speech. Words selected for use according to the present invention usually carry a well defined emotional meaning. For example, "anger" is an English language word that may be used according to the present invention, while the word "regna" is not; the latter carrying no meaning, emotional or otherwise, to most English speakers.

The term "tone" refers in the present invention to a sound characterized by a certain dominant frequency. Several tones are defined by frequency in Table 1 of WO 2007/072485. Among them, for example, are the tones named FA and SOL.

The term "intonation" refers in the present invention to a tone or a set of tones, produced by the vocal chords of a human speaker or an animal. For example the word "love" may be pronounced by a human speaker with such an intonation so that the tones FA and SOL are dominant.

The term "dominant tones" refers in the present invention to tones produced by the speaker with more energy and intensity than other tones. The magnitude or intensity of intonation can be expressed as a table, or graph, relating relative magnitude (measured, for example, in units of dB) to frequency (measured, for example, in units of HZ.)

The term "reference intonation", as used in the present invention, relates to an intonation that is commonly used by many speakers while pronouncing a certain word or, it relates to an intonation that is considered the normal intonation for pronouncing a certain word. For example, the intonation FA SOL may be used as a reference intonation for the word "love" because many speakers will use the FA-SOL intonation when pronouncing the word "love".

The term "emotional attitude", as used in the present invention, refers to an emotion felt by the speaker, and possibly affecting the behavior of the speaker, or predisposing a speaker to act in a certain manner. It may also refer to an instinct driving an animal. For example "anger" is an emotion that may be felt by a speaker and "angry" is an emotional attitude typical of a speaker feeling this emotion.

The term "emotionbase", as used in the present invention, refers to an organized collection of human emotions. The emotions are typically organized to model aspects of reality in a way that supports processes requiring this information. For example, modeling archived assigned referenced emotional attitudes with predefined situations in a way that supports monitoring and managing one's physical, mental and emotional well-being, and subsequently significantly improve them.

The term "architecture", as used in the present invention, refers to a set of disciplines that describes an emotionbase system by specifying its parts and their relations regarding. For example, at a high level, collective emotional architecture may be concerned with how the central processing unit (CPU) acts and how it uses computer memory to archive emotional attitudes.

The term "configure", as used in the present invention, refers to designing, establishing, modifying, or adapting emotional attitudes to form a specific configuration or for some specific purpose, for example in a form of collective emotional architecture.

The term "individual" refers to a person attempting to configure one's collective emotional architecture by evaluating manifestations of physiological change in said individual's voice based on ongoing activity analysis of three neurotransmitter loops, or SHG profile.

The term "SHG" refers to a model for instinctive decision-making that uses a three-dimensional personality profile. The three dimensions are the result of three drives: (1) Survival (S)—the willingness of an individual to fight for his or her own survival and his or her readiness to look out for existential threats; (2) Homeostasis (H) [or "Relaxation"]—the extent to which an individual would prefer to maintain his or her 'status quo' in all areas of life (from unwavering opinions to physical surroundings) and to maintain his or her way of life and activity; and (3) Growth (G)—the extent to which a person strives for personal growth in all areas (e. g., spiritual, financial, health, etc.). It is believed that these three drives have a biochemical basis in the brain by the activity of three neurotransmitter loops: (1) Survival could be driven by the secretion of adrenaline and noradrenalin; (2) Homeostasis could be driven by the secretion of acetylcholine and serotonin; (3) Growth could be driven by the secretion of dopamine. While all human beings share these three instinctive drives (S,H,G), people differ in the relative strengths of the individual drives. For example, a person with a very strong (S) drive will demonstrate aggressiveness, possessiveness and a tendency to engage in high-risk behavior when he or she is unlikely to be caught. On the other hand, an individual with a weak (S) drive will tend to be indecisive and will avoid making decisions. A person with a strong (H) drive will tend to be stubborn and resistant to changing opinions and/or habits. In contrast, an individual with a weak (H) drive will frequently change his or her opinions and/or habits. Or, for example, an individual with a strong (G) drive will strive to learn new subjects and will strive for personal enrichment (intellectual and otherwise). A weak (G) drive, on the other hand, may lead a person to seek isolation and may even result in mental depression.

The principles, systems and methods for determining the emotional subtext of a spoken utterance used in this invention are those disclosed by Levanon et al. in PCT Application WO 2007/072485; a detailed description of their method of intonation analysis may be found in that source. Reference is made to FIG. 1, presenting a schematic and generalized presentation of the basic method for concurrently transmitting a spoken utterance and the speaker's emotional attitudes as determined by intonation analysis [100]. An input module [110] is adapted to receive voice input and orientation reference selected from a group consisting of: date [150], time [160], location [170] and converts sound into a signal such as an electrical or optical signal, digital or analog. The voice recorder typically comprises a microphone. The signal is fed to computer or processor [120] running software code [150] which accesses a emotionbase [140]. According to one embodiment of the system, the computer comprises a personal computer. According to a specific embodiment of the present invention the computer comprises a digital signal processor embedded in a portable device. Emotionbase [140] comprises definitions of certain tones and a glossary relating tones to emotions, stores and archives said emotions. Processing comprises calculating a plurality of dominant tones, and comparing said plurality of dominant tones to a plurality of normal dominant tones specific to a word or set of words pronounced by said individual [170] so as to indicate at least one emotional attitude of said individual [170]. The results of the computation and signal processing are displayed by indicator [130] connected to the computer. According to one specific embodiment of the present invention, the indicator [130] comprises a visual display of text or graphics. According to another specific embodiment of the present invention, it comprises an audio output such as sounds or spoken words. The results of the computation are used for monitoring and managing of risk behaviors [180a]; anxiety, and impulse control disorders [180b]; chronic and acute conditions [180c], thus providing a crucial information for said individual [170] to significantly improve one's mental and emotional well-being.

Figure 2:
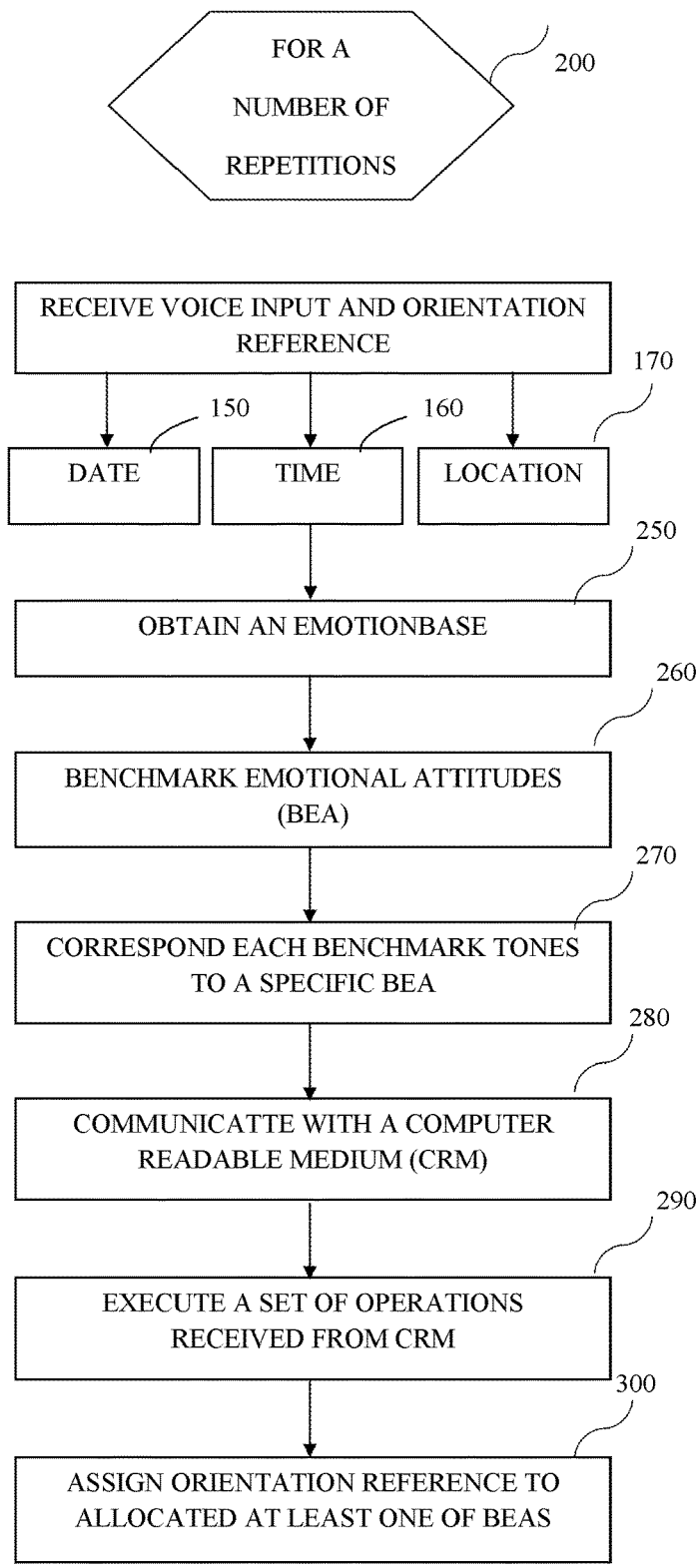
FIG. 2 is a flow diagram illustrating a method for configuring collective emotional architecture of an individual.

Reference is now made to FIG. 2, presenting a flow diagram illustrating a method for configuring collective emotional architecture of an individual. Said method comprises, for a predetermined number of repetitions [200], steps of receiving voice input and an orientation reference [210] selected from a group consisting of date [150], time [160], location [170], and any combination thereof; obtaining an emotionbase [250]; said emotionbase comprising benchmark tones and benchmark emotional attitudes (BEA) [260], each of said benchmark tones corresponds to a specific BEA [270]; at least one processor in communication with a computer readable medium (CRM) [280], said processor executes a set of operations received from said CRM [290]; said set of operations are: (1) obtaining a signal representing sound volume as a function of frequency from said volume input; (2) processing said signal so as to obtain voice characteristics of said individual, said processing includes determining a Function A; said Function A being defined as the average or maximum sound volume as a function of sound frequency, from within a range of frequencies measured in said volume input; said processing further includes determining a Function B; said Function B defined as the averaging, or maximizing of said function A over said range of frequencies and dyadic multiples thereof; (3) comparing said voice characteristics to said benchmark tones; and (4) allocating to said voice characteristics at least one of said BEAs corresponding to said benchmark tones; wherein said method additionally comprises a step of assigning said orientation reference to said allocated at least one of said BEAs [300].

Figure 3:
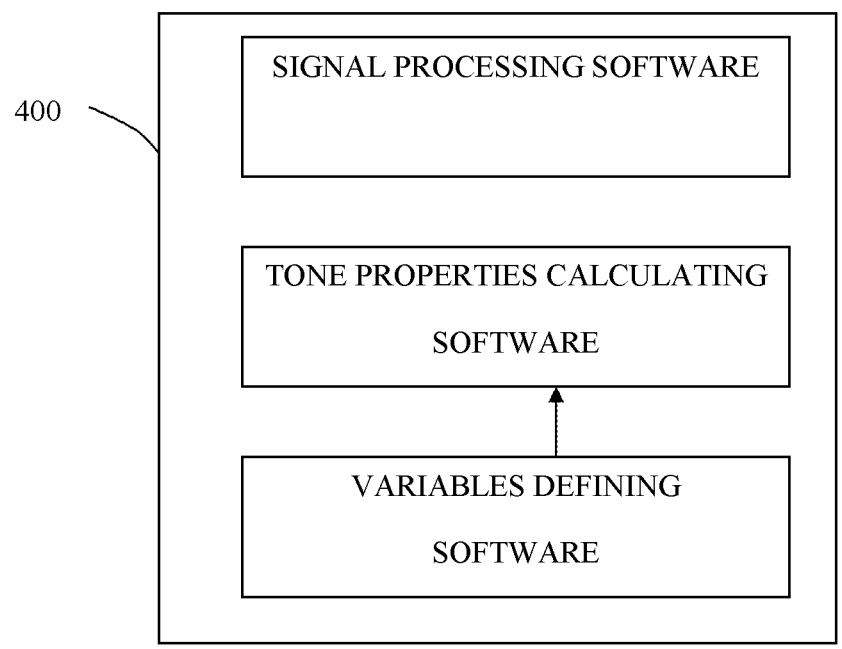
FIG. 3 presents schematically the main software modules in a system according to the present invention.

Reference is now made to FIG. 3, presenting a schematic and generalized presentation of the software [150] of the aforementioned system for communicating emotional attitudes of an individual through intonation. For the sake of clarity and brevity, infrastructure software, e.g. the operating system, is not described here in detail. The relevant software comprises three main components: (1) the signal processing component processes the audio signal received from the recorder and produces voice characteristics such as frequency, amplitude and phase; (2) the software component responsible for tonal characteristics calculations identifies the frequency ranges in which sound amplitude reaches maximum levels, and compares them to reference values found in a glossary of words and tones stored in the database; and (3) the variable definition software component, which defines the intonation specific to the individual [170] and defines the individual's [170] emotional attitudes accordingly.

Figure 4:
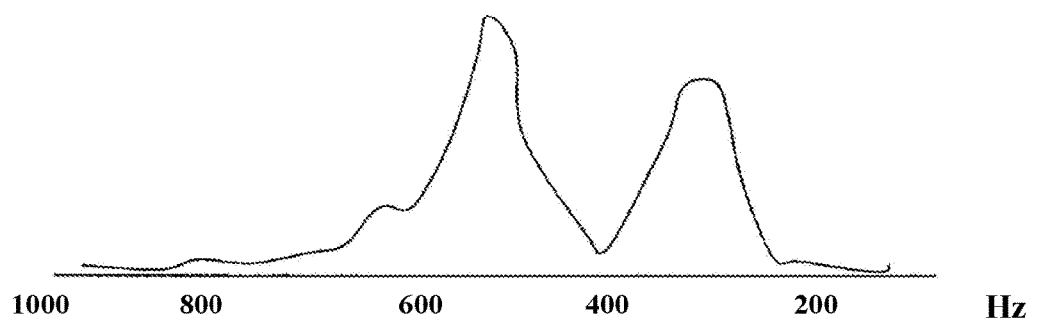
FIG. 4 and FIG. 5 elucidate and demonstrate intonation and its independence of language.
Figure 5:
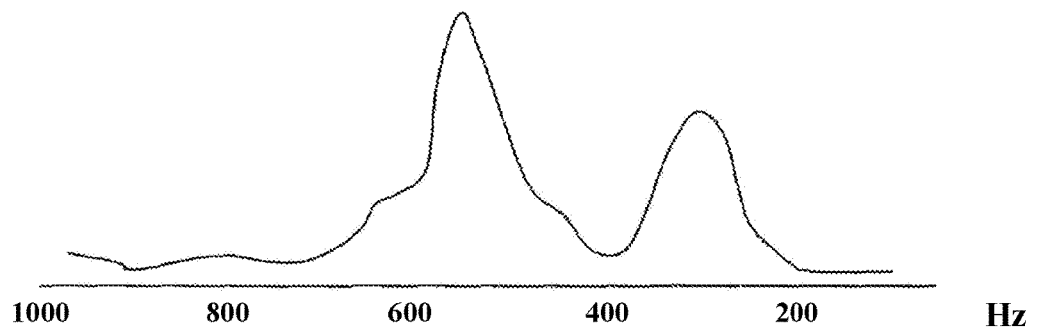

Reference is now made to FIG. 4 and FIG. 5, presenting some research data to elucidate and demonstrate the use of the present invention for indicating emotional attitudes of an individual through intonation analysis. Both figures show a graph of relative sound volume versus sound frequency from 0 to 1000 HZ. Such sound characteristics can be obtained from processing sound as described in reference to FIG. 2, by signal processing software described in reference to FIG.

3, and by equipment described in reference to FIG. 1. The graphs are the result of processing 30 seconds of speech each. Dominant tones can be identified in FIGS. 4 and 5, and the dominant tones in 5a are similar to those of 5b. Both graph result from speaking a word whose meaning is 'love'. The language was Turkish in case of FIG. 4, and English for FIG. 5. Thus these figures demonstrate the concept on dominant tones and their independence of language.

What is claimed is:

1. A system for configuring collective emotional architecture of an individual, said system comprising:
   a. an input module, said input module is adapted to receive voice input and orientation reference selected from a group consisting of: date, time, and location corresponding to said voice input, and any combination thereof;
   b. a personal collective emotionbase; said emotionbase comprising benchmark tones and benchmark emotional attitudes (BEA), each of said benchmark tones corresponds to a specific BEA;
   c. at least one processor in communication with a computer readable medium (CRM), said processor executes a set of operations received from said CRM, said set of operations comprising steps of:
      i. obtaining a signal representing sound volume as a function of frequency from said voice input;
      ii. processing said signal so as to obtain voice characteristics of said individual, said processing includes determining a Function A; said Function A being defined as the average or maximum sound volume as a function of sound frequency, from within a range of frequencies measured in said voice input; said processing further includes determining a Function B; said Function B defined as the averaging, or maximizing of said function A over said range of frequencies and dyadic multiples thereof; and
      iii. comparing said voice characteristics to said benchmark tones;
      iv. assigning to said voice characteristics at least one of said BEAs corresponding to said benchmark tones;
   wherein said set of operations additionally comprises steps of
      v. assigning said orientation reference to said assigned at least one of said BEAs; and
      vi. archiving said assigned at least one orientation reference and said assigned at least one BEA to said emotionbase.

2. The system of claim 1, wherein said archived at least one BEA is stored digitally.

3. The system of claim 2, wherein said digitally stored archived BEA is reported to the individual upon demand independent of the said time corresponding to the voice input and of a time when said set of operations was executed.

4. The system of claim 1, wherein said set of operations additionally comprises a step of matching said archived assigned at least one orientation reference and said archived assigned at least one BEA with predefined situations.

5. The system of claim 4, wherein said set of operations additionally comprises a step of predicting emotional attitude according to records of said matching.

6. The system of claim 5, wherein said set of operations additionally comprises a step of prompting actions relevant to said predicted emotional attitudes.

7. The system of claim 1, wherein said system additionally comprises an output module; said output module is adapted to provide said individual a feedback regarding at least one selected from a group consisting of: his emotional attitude, suggestions how to change his emotional attitude, and suggestions how to avoid a specific emotional attitude.

8. The system of claim 1, wherein said operation of processing comprises identifying at least one dominant tone, and attributing an emotional attitude to said individual based on said at least one dominant tone.

9. The system of claim 1, wherein said operation of processing comprises calculating a plurality of dominant tones, and comparing said plurality of dominant tones to a plurality of normal dominant tones specific to a word or set of words pronounced by said individual so as to indicate at least one emotional attitude of said individual.

10. The system of claim 1, wherein said range of frequencies is between 120 Hz and 240 Hz and all dyadic multiples thereof.

11. The system of claim 1, wherein said operation of comparing comprises calculating the variation between said voice characteristics and tone characteristics related to said benchmark tones.

12. The system of claim 4, wherein said benchmark emotional attitudes (BEA) are analyzed by evaluating manifestations of physiological change in the human voice; said evaluation is based on ongoing activity analysis of three neurotransmitter loops, or SHG profile.

13. The system of claim 4, wherein said system is used for monitoring of risk behaviors; said risk behaviors are selected from a group consisting of: tobacco, alcohol, drug use, eating disorders, gambling addiction, risky sexual behavior, shopping addiction; any other impulse control disorders and addictions and any combination thereof.

14. The system of claim 4, wherein said system is used for managing of risk behaviors; said risk behaviors are selected from a group consisting of: tobacco, alcohol, drug use, eating disorders, gambling addiction, risky sexual behavior, shopping addiction; any other impulse control disorders and addictions and any combination thereof.

15. The system of claim 4, wherein said system is used for monitoring of anxiety, mood (e.g., depression) and impulse control disorders; and any combination thereof.

16. The system of claim 4, wherein said system is used for managing of anxiety, mood (e.g., depression) and impulse control disorders; and any combination thereof.

17. The system of claim 4, wherein said system is used for monitoring of chronic and acute conditions; said chronic and acute conditions are selected from a group consisting of: obesity, diabetes, cardiovascular disease, HIV/STIs; any other chronic and acute conditions and any combination thereof.

18. The system of claim 4, wherein said system is used for managing of chronic and acute conditions; said chronic and acute conditions are selected from a group consisting of: obesity, diabetes, cardiovascular disease, HIV/STIs; any other chronic and acute conditions and any combination thereof.

19. A method for configuring a collective emotional architecture of an individual, said method comprising steps of:
   a. receiving voice input and an orientation reference selected from a group consisting of date, time, and location corresponding to said voice input, and any combination thereof;
   b. obtaining an emotionbase; said emotionbase comprising benchmark tones and benchmark emotional attitudes (BEA), each of said benchmark tones corresponds to a specific BEA;

c. a executing a set of operations received from a computer readable medium (CRM), by at least one processor in communication with said CRM; said set of operations comprises:
  i. obtaining a signal representing sound volume as a function of frequency from said voice input;
  ii. processing said signal so as to obtain voice characteristics of said individual, said processing includes determining a Function A; said Function A being defined as the average or maximum sound volume as a function of sound frequency, from within a range of frequencies measured in said voice input; said processing further includes determining a Function B; said Function B defined as the averaging, or maximizing of said function A over said range of frequencies and dyadic multiples thereof;
  iii. comparing said voice characteristics to said benchmark tones; and
  iv. assigning to said voice characteristics at least one of said BEAs corresponding to said benchmark tones;
 wherein said method additionally comprises steps of
  v. assigning said orientation reference to said assigned at least one of said BEAs; and
  vi. archiving said assigned at least one orientation reference and said assigned at least one BEA to said emotionbase.

20. The method of claim 19, wherein said emotional attitudes are retrieved and stored digitally.

21. The method of claim 20, wherein said digitally stored archived BEA is reported to the individual upon demand independent of said time corresponding to the voice input and of a time when said set of operations was executed.

22. The method of claim 19, wherein said method additionally comprises a step of matching said archived assigned at least one orientation reference and at least one BEA with predefined situations.

23. The method of claim 22, wherein said method additionally comprises a step of predicting emotional attitude according to records of said matching.

24. The method of claim 23, wherein said method additionally comprises a step of prompting actions relevant to said predicted emotional attitudes.

25. The method of claim 19, wherein said method additionally comprises a step of providing said individual a feedback regarding at least one selected from a group consisting of: one's emotional attitude, suggestions how to change one's emotional attitude, and suggestions how to avoid a specific emotional attitude.

26. The method of claim 19, wherein said step of processing comprises identifying at least one dominant tone, and attributing an emotional attitude to said individual based on said at least one dominant tone.

27. The method of claim 19, wherein said step of processing comprises calculating a plurality of dominant tones, and comparing said plurality of dominant tones to a plurality of normal dominant tones specific to a word or set of words pronounced by said individual so as to indicate at least one emotional attitude of said individual.

28. The method of claim 19, wherein said range of frequencies is between 120 Hz and 240 Hz and all dyadic multiples thereof.

29. The method of claim 19, wherein said step of comparing comprises calculating the variation between said voice characteristics and tone characteristics related to said benchmark tones.

30. The method of claim 22, wherein said benchmark emotional attitudes (BEA) are analyzed by evaluating manifestations of physiological change in the human voice; said evaluation is based on ongoing activity analysis of three neurotransmitter loops, or SHG profile.

31. The method of claim 22, wherein said method is used for monitoring of risk behaviors; said risk behaviors are selected from a group consisting of: tobacco, alcohol, drug use, eating disorders, gambling addiction, risky sexual behavior, shopping addiction; any other impulse control disorders and addictions and any combination thereof.

32. The method of claim 22, wherein said method is used for managing of risk behaviors; said risk behaviors are selected from a group consisting of: tobacco, alcohol, drug use, eating disorders, gambling addiction, risky sexual behavior, shopping addiction; any other impulse control disorders and addictions and any combination thereof.

33. The method of claim 22, wherein said method is used for monitoring of anxiety, mood (e.g., depression) and impulse control disorders; and any combination thereof.

34. The method of claim 22, wherein said method is used for managing of anxiety, mood (e.g., depression) and impulse control disorders; and any combination thereof.

35. The method of claim 22, wherein said method is used for monitoring of chronic and acute conditions; said chronic and acute conditions are selected from a group consisting of: obesity, diabetes, cardiovascular disease, HIV/STIs; any other chronic and acute conditions and any combination thereof.

36. The method of claim 22, wherein said method is used for managing of chronic and acute conditions; said chronic and acute conditions are selected from a group consisting of: obesity, diabetes, cardiovascular disease, HIV/STIs; any other chronic and acute conditions and any combination thereof.

37. A system for configuring collective emotional architecture of an individual, said system comprising:
  a. an input module, said input module is adapted to receive voice input and orientation reference selected from a group consisting of: date, time, and location corresponding to said voice input, and any combination thereof;
  b. a personal collective emotionbase; said emotionbase comprising benchmark tones and benchmark emotional attitudes (BEA), each of said benchmark tones corresponds to a specific BEA;
  c. at least one processor in communication with a computer readable medium (CRM), said processor executes a set of operations received from said CRM, said set of operations comprising steps of:
    i. obtaining a signal representing sound volume as a function of frequency from said voice input;
    ii. processing said signal so as to obtain voice characteristics of said individual, said processing includes determining a Function A; said Function A being defined as the average or maximum sound volume as a function of sound frequency, from within a range of frequencies measured in said voice input; said processing further includes determining a Function B; said Function B defined as the averaging, or maximizing of said function A over said range of frequencies and dyadic multiples thereof; and
    iii. comparing said voice characteristics to said benchmark tones;
    iv. assigning to said voice characteristics at least one of said BEAs corresponding to said benchmark tones;
   wherein said set of operations additionally comprises a steps of assigning said orientation reference to said assigned at least one of said BEAs; and wherein said system additionally comprises an output module; said output module is adapted to provide said individual a feedback regarding at least one selected from a group consisting of: his emotional attitude, suggestions how to change his emotional attitude, and suggestions how to avoid a specific emotional attitude.

38. A method for configuring a collective emotional architecture of an individual, said method comprising steps of:
   a. receiving voice input and an orientation reference selected from a group consisting of date, time, and location corresponding to said voice input, and any combination thereof;
   b. obtaining an emotionbase; said emotionbase comprising benchmark tones and benchmark emotional attitudes (BEA), each of said benchmark tones corresponds to a specific BEA;
   c. executing a set of operations received from a computer readable medium (CRM), by at least one processor in communication with said CRM; said set of operations comprises:
      i. obtaining a signal representing sound volume as a function of frequency from said voice input;
      ii. processing said signal so as to obtain voice characteristics of said individual, said processing includes determining a Function A; said Function A being defined as the average or maximum sound volume as a function of sound frequency, from within a range of frequencies measured in said voice input; said processing further includes determining a Function B; said Function B defined as the averaging, or maximizing of said function A over said range of frequencies and dyadic multiples thereof;
      iii. comparing said voice characteristics to said benchmark tones; and
      iv. assigning to said voice characteristics at least one of said BEAs corresponding to said benchmark tones;
   wherein said method additionally comprises a steps of
      v. assigning said orientation reference to said assigned at least one of said BEAs; and
      vi. providing said individual a feedback regarding at least one selected from a group consisting of: one's emotional attitude, suggestions how to change one's emotional attitude, and suggestions how to avoid a specific emotional attitude.

* * * * *